US008544723B2

(12) United States Patent
Yamano et al.

(10) Patent No.: US 8,544,723 B2
(45) Date of Patent: Oct. 1, 2013

(54) AUTOMATIC ANALYZER WITH THE FUNCTION OF RENDERING REAGENT INFORMATION UNREADABLE

(75) Inventors: Teruhiro Yamano, Hitachinaka (JP); Yoshimitsu Takagi, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 13/322,166

(22) PCT Filed: May 14, 2010

(86) PCT No.: PCT/JP2010/003258
§ 371 (c)(1),
(2), (4) Date: Dec. 14, 2011

(87) PCT Pub. No.: WO2010/140303
PCT Pub. Date: Dec. 9, 2010

(65) Prior Publication Data
US 2012/0080516 A1    Apr. 5, 2012

(30) Foreign Application Priority Data
Jun. 2, 2009   (JP) .................................. 2009-132653

(51) Int. Cl.
*G06F 17/00*    (2006.01)
*G06K 7/10*    (2006.01)

(52) U.S. Cl.
USPC ................. 235/375; 235/462.01; 235/462.14; 235/494

(58) Field of Classification Search
USPC ................ 235/375, 462.01–462.1, 462.14, 235/462.15, 494; 422/64–102
See application file for complete search history.

(56) References Cited

U.S. PATENT DOCUMENTS

| | | | |
|---|---|---|---|
| 6,736,312 B2 * | 5/2004 | Komurasaki et al. | 235/375 |
| 7,114,655 B2 * | 10/2006 | Chapman et al. | 235/462.01 |
| 2004/0109682 A1 * | 6/2004 | Hall | 396/567 |
| 2004/0258565 A1 * | 12/2004 | Watari | 422/64 |
| 2005/0084426 A1 * | 4/2005 | Mimura et al. | 422/102 |
| 2006/0168661 A1 * | 7/2006 | Kisley et al. | 726/26 |
| 2007/0255756 A1 | 11/2007 | Satomura et al. | |
| 2007/0266210 A1 * | 11/2007 | Hwang et al. | 711/154 |
| 2008/0233012 A1 | 9/2008 | Zander | |
| 2009/0134978 A1 * | 5/2009 | Imai | 340/10.6 |

(Continued)

FOREIGN PATENT DOCUMENTS

| | | |
|---|---|---|
| JP | 9-26425 A | 1/1997 |
| JP | 2006-146620 A | 6/2006 |
| JP | 2008-233087 A | 10/2008 |
| WO | 2006/009251 A1 | 1/2006 |

*Primary Examiner* — Tuyen K Vo
(74) *Attorney, Agent, or Firm* — Mattingly & Malur, PC

(57) ABSTRACT

The invention provides an automatic analyzer suitable for efficient reagent management. The analyzer allows continued use of existing reagent information storage media because reagent ID information that is no longer needed is overwritten so that it is unrecognizable to any analyzer. The invention relates to a method for automatically analyzing particular properties of an analyte by putting the analyte and a reagent into a vessel and measuring the reacted analyte-reagent mixture. The analyzer of the invention comprises: an information reader/writer for reading or writing regent information to/from storage media attached to reagent vessels; means for managing reagent information read from the storage media; means for processing reagents based on the managed information; and means for overwriting reagent information that has been judged unnecessary based on the managed information so that the unnecessary information is unrecognizable to any analyzer.

4 Claims, 7 Drawing Sheets

(56) References Cited

U.S. PATENT DOCUMENTS

2010/0188244 A1* 7/2010 Sattler et al. ............... 340/686.1
2010/0288830 A1* 11/2010 Watari ......................... 235/375
2011/0095864 A1* 4/2011 Trueeb et al. ................ 340/10.1

* cited by examiner

FIG. 5

| HIGH 4 BITS → <br> ↓ LOW 4 BITS | 0 (0000) | 1 (0001) | 2 (0010) | 3 (0011) | 4 (0100) | 5 (0101) | 6 (0110) | 7 (0111) |
|---|---|---|---|---|---|---|---|---|
| 0(0000) | NUL | DLE | SP | 0 | @ | P | ` | p |
| 1(0001) | SOH | DC1 | ! | 1 | A | Q | a | q |
| 2(0010) | STX | DC2 | " | 2 | B | R | b | r |
| 3(0011) | ETX | DC3 | # | 3 | C | S | c | s |
| 4(0100) | EOT | DC4 | $ | 4 | D | T | d | t |
| 5(0101) | ENQ | NAC | ％ | 5 | E | U | e | u |
| 6(0110) | ACK | SYN | & | 6 | F | V | f | v |
| 7(0111) | BEL | ETB | ' | 7 | G | W | g | w |
| 8(1000) | BS | CAN | ( | 8 | H | X | h | x |
| 9(1001) | HT | EM | ) | 9 | I | Y | i | y |
| 10(1010) | LF/NL | SUB | * | : | J | Z | j | z |
| 11(1011) | VT | ESC | + | ; | K | [ | k | { |
| 12(1100) | FF | FS | , | < | L | ¥ | l | \| |
| 13(1101) | CR | GS | - | = | M | ] | m | } |
| 14(1110) | SO | RS | . | > | N | ^ | n | ~ |
| 15(1111) | SI | US | / | ? | O | _ | o | DEL |

FIG. 6

| HIGH 4 BITS → <br> ↓ LOW 4 BITS | 0 <br> (0000) | 1 <br> (0001) | 2 <br> (0010) | 3 <br> (0011) |
|---|---|---|---|---|
| 0 (0000) | 0 | G | W | m |
| 1 (0001) | 1 | H | X | n |
| 2 (0010) | 2 | I | Y | o |
| 3 (0011) | 3 | J | Z | p |
| 4 (0100) | 4 | K | a | q |
| 5 (0101) | 5 | L | b | r |
| 6 (0110) | 6 | M | c | s |
| 7 (0111) | 7 | N | d | t |
| 8 (1000) | 8 | O | e | u |
| 9 (1001) | 9 | P | f | v |
| 10 (1010) | A | Q | g | w |
| 11 (1011) | B | R | h | x |
| 12 (1100) | C | S | i | y |
| 13 (1101) | D | T | j | z |
| 14 (1110) | E | U | k | |
| 15 (1111) | F | V | l | |

FIG. 7

| CONDITION CODE | CONDITION THAT MAKES THE REAGENT UNUSABLE | |
|---|---|---|
| 1 | PROBLEM WITH AMOUNT LEFT | SHORTAGE |
| 2 | | DEGRADED PERFORMANCE DUE TO ADDITIONAL REAGENT FILLING |
| 3 | | DISAGREEMENT IN LIQUID SURFACE LEVEL DUE TO REAGENT SPILL |
| 4 | | BUBBLES ON THE REAGENT SURFACE |
| 5 | | DETECTION OF IMPURITIES |
| 6 | PROBLEM WITH EXPIRATION DATE | EXPIRATION DATE PASSED |
| 7 | | USABLE PERIOD PASSED AFTER REAGENT OPENING |
| 8 | PROBLEM WITH REAGENT STORAGE | INSUFFICIENT TEMPERATURE CONTROL |
| 9 | | INSUFFICIENT HUMIDITY CONTROL |
| 10 | | INSUFFICIENT LIGHT SHIELDING |
| 11 | REAGENT DETERIORATION | CALIBRATION FAILURE |
| 12 | | CONTROL MEASUREMENT VALUES BEYOND ACCEPTABLE RANGE |

FIG. 8

$$x_i = a_i + b_i \cdot 2^7 \quad (i = 1, 2, \cdots, m) \quad \cdots \text{EQUATION 1}$$

$x_i$ : THE iTH BYTE INFORMATION OF COMPOSITE INFORMATION
$a_i$ : THE iTH ASCII CHARACTER OF REAGENT ID INFORMATION
$b_i$ : THE iTH BIT VALUE OF ADDITIONAL INFORMATION
m : THE CHARACTER LENGTH OF REAGENT ID INFORMATION

FIG. 9

$$a_i = (x_i << 1) >> 1 \quad \cdots \text{EQUATION 2}$$
$$b_i = a_i >> 7 \quad \cdots \text{EQUATION 3}$$

NOTE : THE SIGN "<<" REPRESENTS THE BITWISE LEFT-SHIFT OPERATOR, AND THE SIGN ">>"REPRESENTS THE BITWISE RIGHT-SHIFT OPERATOR.

FIG. 10

$$x_i = T(a_i) + b_{2i} \cdot 2^7 + b_{2i-1} \cdot 2^6 \quad (i = 1, 2, \cdots, m) \quad \cdots \text{EQUATION 4}$$

$x_i$ : THE iTH BYTE INFORMATION OF COMPOSITE INFORMATION
$a_i$ : THE iTH ASCII CHARACTER OF REAGENT ID INFORMATION
$b_{2i}$ : THE (2i)TH BIT VALUE OF ADDITIONAL INFORMATION
$b_{2i-1}$ : THE (2i-1)TH BIT VALUE OF ADDITIONAL INFORMATION
m : THE CHARACTER LENGTH OF REAGENT ID INFORMATION
NOTE : THE SIGN "T(a)" REPRESENTS A FUNCTION FOR CONVERTING AN ASCII CHARACTER INTO ITS CORRESPONDING BINARY CODE BASEDON AN ALPHANUMERIC CONVERSION TABLE

FIG. 11

$$a_i = T^{-1}((x_i << 2) >> 2) \quad \cdots \text{EQUATION 5}$$
$$b_{2i-1} = a_i >> 7 \quad \cdots \text{EQUATION 6}$$
$$b_{2i} = (a_i << 1) >> 7 \quad \cdots \text{EQUATION 7}$$

NOTE : THE SIGN "$T^{-1}(a)$" REPRESENTS A FUNCTION FOR CONVERTING A BINARY CODE INTO ITS CORRESPONDING ASCII CHARACTER BASED ON AN ALPHANUMERIC CONVERSION TABLE

AUTOMATIC ANALYZER WITH THE FUNCTION OF RENDERING REAGENT INFORMATION UNREADABLE

TECHNICAL FIELD

The present invention relates to an automatic analyzer that exchanges information with the reagent information storage media attached to reagent vessels.

BACKGROUND ART

JP-9-26425-A discloses a reagent management technique for an automatic analyzer. To identify a reagent, the analyzer reads reagent ID information from the storage medium attached to its vessel and searches the reagent information database stored on the analyzer for the reagent with the matched ID. By doing so, the analyzer judges whether the reagent has already been registered or not yet. If the reagent needs to be newly registered, necessary information is stored for its management, such as its remaining amount and expiration date. If the reagent has already been registered, its management is continued using already stored information such as its remaining amount and expiration date.

International Publication No. WO/2006/009251 also discloses a reagent management technique in which reagent information storage media are designed to store reagent information including information that is used to render reagents unusable.

Such reagent information is collectively managed by a server system with the use of reagent IDs or simply stored on reagent information storage media together with reagent IDs, or both of these methods are used at the same time.

Whatever the method, conventional reagent management often requires the use of reagent IDs to identify reagents as well as the writing or reading of reagent information to/from storage media.

Collective management of reagent IDs using a server system involves higher data transfer costs, compared with the method of storing reagents IDs on storage media together with reagent information.

Nevertheless, there are also problems with the latter method. First, it is difficult to collect widely distributed reagent information storage media and redistribute them after adding new reagent information. Moreover, even if the auxiliary data areas of those storage media have been used as reagent information areas for storing the new reagent information, reading that information requires the modification and redistribution of analyzer software for information readers to read the new information. Thus, if the software modification is not done, new reagent information cannot be added, or a reagent that has been judged unusable may be able to be used by certain analyzers.

PRIOR ART LITERATURE

Patent Document

Patent Document 1: JP-9-26425-A
Patent Document 2: WO/International Publication No. 2006/009251

SUMMARY OF THE INVENTION

Problems to be Solved by the Invention

The present invention provides a method for storing information on reagent information storage media. The method allows continued use of reagent information storage media that have already been distributed widely. Also, when a reagent whose vessel has such a storage medium is judged unusable, the method prevents any analyzer from using this reagent. In addition, the method allows storage of the information that was used to judge that reagent unusable.

Means for Solving the Problems

The primary feature of the invention is that when the reagent ID stored on a reagent information storage medium is rendered unidentifiable, the reagent ID cannot be interpreted by an information reader even if the reader tries to read the reagent ID.

Effects of the Invention

By rendering the information of a reagent unidentifiable to make the reagent unusable, an automatic analyzer is prevented from using that reagent even when the analyzer reads its reagent ID from its reagent information storage medium. Because the information areas in which reagent IDs are stored are used, the present invention allows use of existing reagent information storage media.

Also, in the event that a reagent information storage medium is rewriteable and that the information constituting the reagent ID stored on the medium has to be within a defined value range, overwriting the reagent ID with information that is out of the range renders the ID unidentifiable. To do so, a bit operation is performed between the stored reagent ID and additional information with the use of equations, so that the result information is out of the defined value range. It is thus possible to store the reagent ID together with the additional information and at the same time render the reagent unusable by making its reagent information unidentifiable.

BRIEF DESCRIPTION OF THE DRAWINGS

FIG. 5 is the ASCII code table;

FIG. 6 is an alphanumeric conversion table;

FIG. 7 shows the codes of conditions that make reagents unusable;

FIG. 8 shows an equation for obtaining composite information from reagent ID information and additional information;

FIG. 9 shows equations for obtaining reagent ID information and additional information from composite information;

FIG. 10 shows an equation for obtaining composite information from reagent ID information and additional information; and FIG. 11 shows equations for obtaining reagent ID information and additional information from composite information.

MODE FOR CARRYING OUT THE INVENTION

A preferred embodiment of the present invention will now be described with reference to the accompanying drawings.

Embodiment 1

Figure 1:
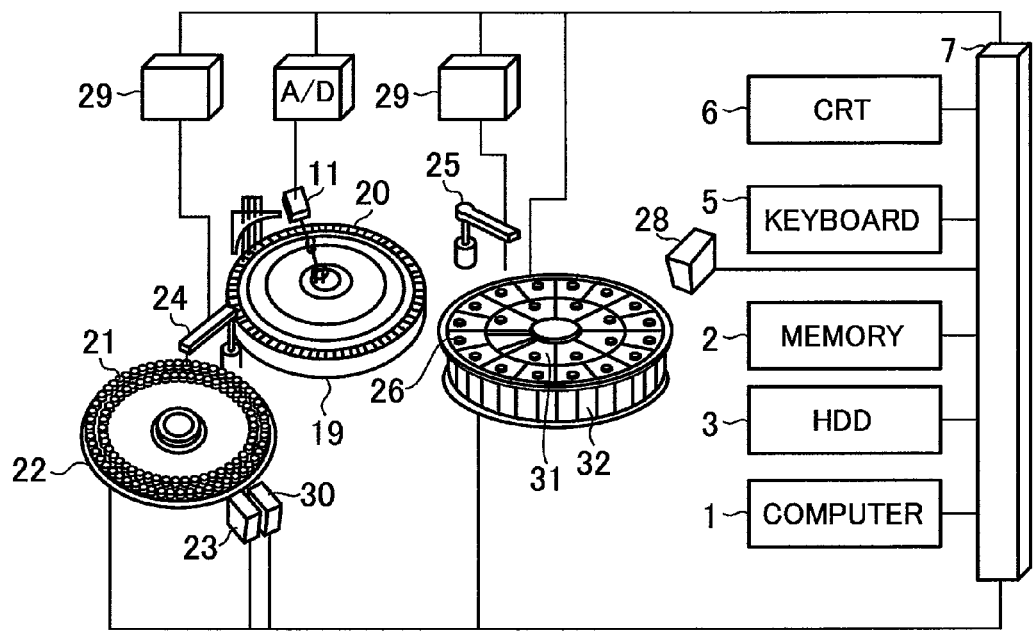
FIG. 1 is a schematic illustrating the overall configuration of an automatic analyzer according to an embodiment of the invention.

FIG. 1 is a schematic illustrating the overall configuration of an automatic chemical analyzer according to Embodiment 1 that examines multiple properties of each sample using photometry.

As illustrated in FIG. 1, a number of sample vessels 21 each containing a sample are arranged on a sample transfer mechanism 22. A sample dispenser 24 suctions a sample from any one of the sample vessels 21 and discharges the sample into one of the reaction vessels 20 arranged a reaction vessel transfer mechanism 19. At the same time, a first reagent transfer mechanism 31 or a second reagent transfer mechanism 32 is moved so that the reagent vessel 26 containing the reagent used for that sample will be moved to the position of a reagent dispenser 25. The reagent dispenser 25 then suctions the reagent and discharges it into the reaction vessel 20 containing the sample, thereby causing a chemical reaction. Thereafter, a photometer 11 measures the absorbance of the resultant substance in this sample vessel 21 to calculate constituent concentrations of the sample.

Figure 2:
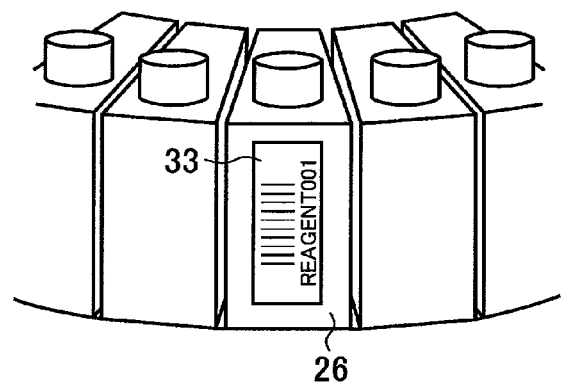
FIG. 2 is a diagram illustrating the external appearance of a reagent information storage medium used for the analyzer of FIG. 1.
Figure 3:
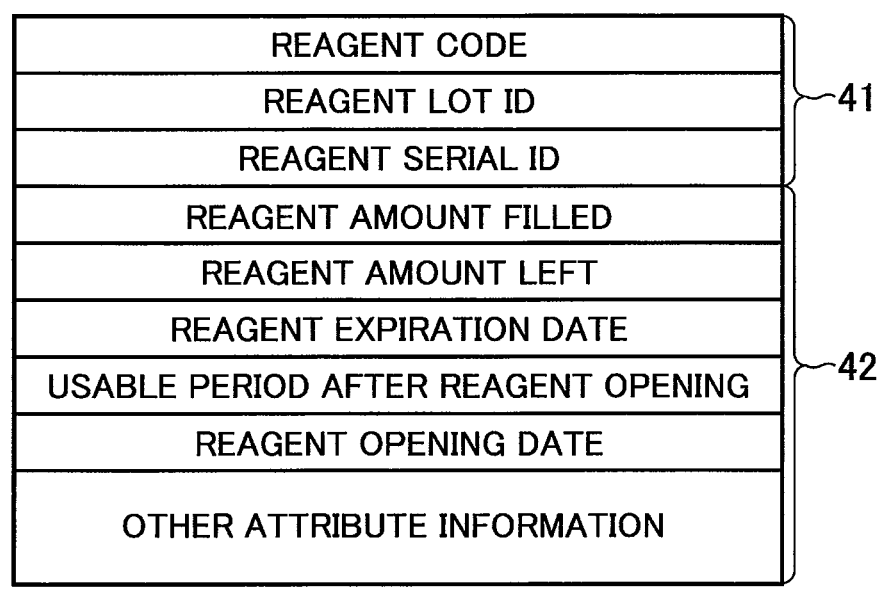
FIG. 3 is a list of information to be stored on the storage medium of FIG. 2.

As also illustrated in FIG. 1, a reagent information reader/writer 28 is installed close to the first and second reagent transfer mechanisms 31 and 32. Further, a number of reagent vessels 26 each containing a regent are arranged on the first and second reagent transfer mechanism 31 and 32. The reader/writer 28 and the first and second reagent transfer mechanism 31 and 32 are all controlled by a microcomputer 1 via an interface 7. The microcomputer 1 is designed to control the operation of each component and perform calculations on measured data. Referring to FIG. 2, a reagent information storage medium 33 is attached to each reagent vessel 26. Each storage medium 33 stores, as shown in FIG. 3, reagent ID information 41 together with reagent attribute information 42.

The following describes how to store such information on a reagent information storage medium 33.

The reagent ID information 41 stored on a storage medium 33 includes the reagent code, the reagent lot ID, and the serial reagent ID and is stored as a bit array according to the well-known ASCII code, which array represents a string of an N number of characters. As shown in the ASCII code table of FIG. 5, the ASCII code defines 7-bit character information, that is, 128 characters (two to the 7th power). Of the 128 characters, 33 characters are control characters, and the rest (95 characters) are non-control characters including alphabetical characters, numbers, symbols, and an invisible space. On computers, the number 0 is placed before the first bit of such 7-bit information, forming 8-bit (i.e., 1-byte) information. For example, the binary notation 01000001(2), equivalent to the hexadecimal notation 41(16), represents the character "A." To represent the character string "AA" in binary notation, then, the notation 01000001(2) is followed by itself, resulting in the notation 0100000101000001(2).

Thus, when the reagent ID information 41 stored on a storage medium 33 is "readable," it means that such 1-byte codes as listed in the ASCII code table are stored on the storage medium 33.

The first bit of such an 8-bit code is used for the definition of part of additional information. Because the reagent ID information 41 stored on a storage medium 33 is a string of an N number of ASCII characters, it can define N-bit additional information, two to the Nth power. Suppose here that the additional information is the value 2, which is 11(2) in binary notation. When this value is combined with the above-mentioned character string "AA" with the use of Equation 1 of FIG. 8, the result is 1100000111000001(2). Because this information is not listed in the ASCII code table, it is unreadable as a reagent ID. The above method of storing the reagent ID information 41 allows the information to be read as a reagent ID and at the same time prevents the information from being read with the use of additional information. The resultant composite information can be reconverted into the original reagent ID using Equation 2 of FIG. 9 and into the additional information using Equation 3 of FIG. 9.

Suppose, for example, that a reagent ID is made up of a 3-digit reagent code, a 3-digit reagent lot ID, and a 3-digit serial reagent ID and also that the reagent ID is defined using any ASCII characters. Thus, the reagent ID is a string of 9 ASCII characters, meaning it can define 9-bit additional information. For instance, of the 9 bits of the additional information, 1 bit can be used to denote the presence or absence of the additional information (1 meaning "present"), 4 bits a reference code, and another 4 bits the manufacturer ID.

The following provides a more specific example.

Reagent code ($x_{123}$): Az1(ASCII)
Reagent lot ID ($x_{456}$): 012(ASCII)
Serial reagent ID ($x_{789}$): 999(ASCII)
Presence or absence of additional information ($b_1$): 1(2)
Reference code ($b_{2345}$): 3(10)=0011(2)
Manufacturer ID ($b_{6789}$): 4(10)=0100(2)

In this case, composite information $x_i$ can be obtained as follows:

$$x_1 = A(\text{ASCII}) + 1 \times 2^7 = 01000001(2) + 10000000(2) = 11000001(2)$$

$$x_2 = z(\text{ASCII}) + 0 \times 2^7 = 01111010(2) + 00000000(2) = 01111010(2)$$

$$x_3 = 1(\text{ASCII}) + 0 \times 2^7 = 00110001(2) + 00000000(2) = 00110001(2)$$

$$x_4 = 0(\text{ASCII}) + 1 \times 2^7 = 00110000(2) + 10000000(2) = 10110000(2)$$

$$x_5 = 1(\text{ASCII}) + 1 \times 2^7 = 00110001(2) + 10000000(2) = 10110001(2)$$

$$x_6 = 2(\text{ASCII}) + 0 \times 2^7 = 00110010(2) + 00000000(2) = 00110010(2)$$

$$x_7 = 9(\text{ASCII}) + 1 \times 2^7 = 00111001(2) + 10000000(2) = 10111001(2)$$

$$x_8 = 9(\text{ASCII}) + 0 \times 2^7 = 00111001(2) + 00000000(2) = 00111001(2)$$

$$x_9 = 9(\text{ASCII}) + 0 \times 2^7 = 00111001(2) + 00000000(2) = 00111001(2)$$

Of the above composite information, at least the value of $x_1$ "11000001(2)" is not an ASCII code, meaning the composite information cannot be read as a reagent ID.

The following shows how to extract reagent ID information from the composite information.

$$a_1 = (11000001(2) << 1) >> 1 = 10000010(2) >> 1 = 01000001(2)$$

$$a_2 = (01111010(2) << 1) >> 1 = 11110100(2) >> 1 = 01111010(2)$$

$$a_3 = (00110001(2) << 1) >> 1 = 01100010(2) >> 1 = 00110001(2)$$

$$a_4 = (10110000(2) << 1) >> 1 = 01100000(2) >> 1 = 00110000(2)$$

$$a_5 = (10110001(2) << 1) >> 1 = 01100010(2) >> 1 = 00110001(2)$$

$a_6 = (00110010(2) << 1) >> 1 = 01100100(2) >> 1 = 00110010(2)$ $a_7 = (10111001(2) << 1) >> 1 = 01110010(2) >> 1 = 00111001(2)$ $a_8 = (00111001(2) << 1) >> 1 = 01110010(2) >> 1 = 00111001(2)$ $a_9 = (00111001(2) << 1) >> 1 = 01110010(2) >> 1 = 00111001(2)$

Likewise, the following shows how to extract the additional information from the composite information.

$b_1 = 11000001(2) >> 7 = 1(2)$ $b_2 = 01111010(2) >> 7 = 0(2)$ $b_3 = 00110001(2) >> 7 = 0(2)$ $b_4 = 10110000(2) >> 7 = 1(2)$ $b_5 = 10110001(2) >> 7 = 1(2)$ $b_6 = 00110010(2) >> 7 = 0(2)$ $b_7 = 10111001(2) >> 7 = 1(2)$ $b_8 = 00111001(2) >> 7 = 0(2)$ $b_9 = 00111001(2) >> 7 = 0(2)$

Alternatively, different equations can be used as discussed below. Assume now that the reagent ID information 41 stored on a storage medium 33 is defined using only alphanumeric characters (not using symbols and the like). In this case, when the reagent ID information 41 is converted into 8-bit codes with the use of the alphanumeric conversion table of FIG. 6, the first 2 bits of each 8-bit code become available to use for the definition of additional information. Because the reagent ID information 41 is a string of an N number of ASCII characters, it can define additional information of N sets of 2 bits (i.e., four to the Nth power). For example, according to the alphanumeric conversion table of FIG. 6, the character string "AA" is converted into 0000101000001010(2). If the additional information is the value 9, which is 1001(2) in binary notation, and it is combined with the character string "AA" with the use of Equation 4 of FIG. 10, the result is 1000101001001010(2).

Suppose, for example, that a reagent ID is made up of a 3-digit reagent code, a 3-digit reagent lot ID, and a 3-digit serial reagent ID and also that the reagent ID is defined using any ASCII characters. Thus, the reagent ID is a string of 9 ASCII characters, meaning it can define 9-bit additional information. For instance, of the 9 bits of the additional information, 1 bit can be used to denote the presence or absence of the additional information (1 meaning "present"), 4 bits a reference code, another 4 bits the manufacturer ID, and 9 bits the device ID.

The following provides a more specific example.
Reagent code ($x_{123}$): Az1(ASCII)
Reagent lot ID ($x_{456}$): 012(ASCII)
Serial reagent ID ($x_{789}$): 999(ASCII)
Presence or absence of additional information ($b_1$): 1(2)
Reference code ($b_{2345}$): 3(10)=0011(2)
Manufacturer ID ($b_{6789}$): 4(10)=0100(2)
Device ID ($b_{10-18}$): 343(10)=101010111(2)

In this case, composite information $x_i$ can be obtained with the use of Equation 4 of FIG. 10 as shown below:

$x_1 = T(A) + 1 \times 2^7 + 0 \times 2^6 = 00001010(2) + 10000000(2) = 10001010(2)$ $x_2 = T(z) + 0 \times 2^7 + 1 \times 2^6 = 00111101(2) + 01000000(2) = 01111101(2)$ $x_3 = T(1) + 1 \times 2^7 + 0 \times 2^6 = 00000001(2) + 10000000(2) = 10000001(2)$ $x_4 = T(0) + 1 \times 2^7 + 0 \times 2^6 = 00000000(2) + 10000000(2) = 10000000(2)$ $x_5 = T(1) + 0 \times 2^7 + 1 \times 2^6 = 00000001(2) + 10000000(2) = 01000001(2)$ $x_6 = T(2) + 0 \times 2^7 + 1 \times 2^6 = 00000010(2) + 01000000(2) = 01000010(2)$ $x_7 = T(9) + 0 \times 2^7 + 1 \times 2^6 = 00001001(2) + 01000000(2) = 01001001(2)$ $x_8 = T(9) + 0 \times 2^7 + 1 \times 2^6 = 00001001(2) + 01000000(2) = 01001001(2)$ $x_9 = T(9) + 1 \times 2^7 + 1 \times 2^6 = 00001001(2) + 11000000(2) = 11001001(2)$ Of the above composite information, at least the value of $x_1$ "10001010(2)" is not an ASCII code, meaning the composite information cannot be read as a reagent ID.

The following shows how to extract reagent ID information from the composite information using Equation 5 of FIG. 11.

$a_1 = T^{-1}((10001010(2) << 2) >> 2) = T^{-1}((00001010(2))) = A(ASCII)$ $a_2 = T^{-1}((01111101(2) << 2) >> 2) = T^{-1}((00111101(2))) = z(ASCII)$ $a_3 = T^{-1}((10000001(2) << 2) >> 2) = T^{-1}((00000001(2))) = 1(ASCII)$ $a_4 = T^{-1}((10000000(2) << 2) >> 2) = T^{-1}((00000000(2))) = 0(ASCII)$ $a_5 = T^{-1}((01000001(2) << 2) >> 2) = T^{-1}((00000001(2))) = 1(ASCII)$ $a_6 = T^{-1}((01000010(2) << 2) >> 2) = T^{-1}((00000010(2))) = 2(ASCII)$ $a_7 = T^{-1}((01001001(2) << 2) >> 2) = T^{-1}((00001001(2))) = 9(ASCII)$ $a_8 = T^{-1}((01001001(2) << 2) >> 2) = T^{-1}((00001001(2))) = 9(ASCII)$ $a_9 = T^{-1}((11001001(2) << 2) >> 2) = T^{-1}((00001001(2))) = 9(ASCII)$

Likewise, the following shows how to extract the additional information from the composite information using Equations 6 and 7 of FIG. 11.

$b_1 = 10001010(2) >> 7 = 1(2)$ $b_2 = (10001010(2) << 1) >> 7 = 0(2)$ $b_3 = 01111101(2) >> 7 = 0(2)$ $b_4 = (01111101(2) << 1) >> 7 = 1(2)$ $b_5 = 10000001(2) >> 7 = 1(2)$ $b_6 = (10000001(2) << 1) >> 7 = 0(2)$ $b_7 = 10000000(2) >> 7 = 1(2)$ $$b_8=(10000000(2)<<1)>>7)=0(2)$$

$$b_9=01000001(2)>>7=0(2)$$

$$b_{10}=(01000001(2)<<1)>>7)=1(2)$$

$$b_{11}=01000010(2)>>7=0(2)$$

$$b_{12}=(01000010(2)<<1)>>7)=1(2)$$

$$b_{13}=01001001(2)>>7=0(2)$$

$$b_{14}=(01001001(2)<<1)>>7)=1(2)$$

$$b_{15}=01001001(2)>>7=0(2)$$

$$b_{16}=(01001001(2)<<1)>>7)=1(2)$$

$$b_{17}=11001001(2)>>7=1(2)$$

$$b_{18}=(11001001(2)<<1)>>7)=1(2)$$

The above-described methods of storing reagent ID information 41 on a storage medium 33 allow the information to be read as a reagent ID or prevent the information from being read with the use of additional information. Also, the resultant composite information can be reconverted into the original reagent ID and into the additional information.

As still another method, reagent ID information 41 can be stored on a storage medium 33 as a bit array comprising N sets of 4-byte integers. Each 4-byte (i.e., 32-bit) integer can store $2^{32}=4,294,967,296$ values.

In this case, when the reagent ID information 41 stored on a storage medium 33 is "readable," it means that such 4-byte integers are stored on the storage medium 33 and that the integers are within the value range of the reagent ID information 41.

Assume, for example, that the value range of the reagent ID information 41 is from 1 to 999,999. Because this can be represented by a 3-byte integer, the first 1 byte of each 4-byte integer can be used for the definition of part of additional information. Since the reagent ID information 41 is an N number of 4-byte integers, it can define N-byte additional information, 256 to the Nth power. If the additional information is the value 2, which is 02(16) in hexadecimal notation, and it is combined with the value 999,999(10), the result is 020F423F(16). This is equivalent to 34,554,431(10) and thus out of the value range of the reagent ID information 41, meaning that it is unreadable as a reagent ID.

As above, we have shown that the reagent ID information 41 stored on a storage medium 33 can be rendered unreadable by combining the ID information 41 with additional information so that the resultant composite information deviates from the value range of the reagent ID information 41. We have also shown that the reagent ID information 41 and the additional information can be extracted from the composite information. What matters are that the composite information deviates from the value range of the reagent ID information 41 and that the reagent ID information 41 and the additional information can be extracted from the composite information. How to add the additional information as well as such equations as mentioned above can be determined as desired. In addition, the composite information does not necessarily have to be read by the automatic analyzer. It is only necessary to collect reagent vessels 26 that have been rendered unusable and examine their causes using an analysis tool.

It is also possible to simply overwrite all the bit information constituting reagent ID information 41 with 0s if it is not necessary to analyze the ID information 41 and its additional information. By doing so, the ID information 41 can be changed into non-ASCII codes and thus rendered unreadable. This is advantageous in terms of software configuration (i.e., simpler software) although it becomes impossible to examine why particular reagent vessels 26 have been rendered unusable. It is further possible to overwrite, with 0s for example, not only the ID information but also all the information stored on particular storage media 33, thereby making it impossible to read any information from those media 33.

Information that can be overwritten also includes such information as can be used for controlling reagent dispensing (e.g., physical information of reagent vessels 26 such as how much the vessels 26 are filled or their bottle shapes). The reason for this is that if the information used for controlling reagent dispensing cannot be analyzed by software, reagent dispensing becomes impossible. If such information is overwritten, reagent ID information need not be overwritten. This is advantages in that the analyzer can still identify each reagent and at the same time prevent those reagents judged unusable from being used. However, how the analyzer will behave when reagent dispensing cannot be controlled depends on the analyzer itself.

Though not illustrated in the drawings, the above-described methods of the invention are applicable not only to reagent ID information but to the ID information of any other liquid as long as it is identifiable and it is the liquid whose remaining amount and expiration date can be kept track of. Examples include sample ID information imparted to sample vessels into which a known amount of a calibrator or control sample has been dispensed; and detergent ID information imparted to detergent vessels which are used for rinsing the liquid passageways of the analyzer.

Figure 4:
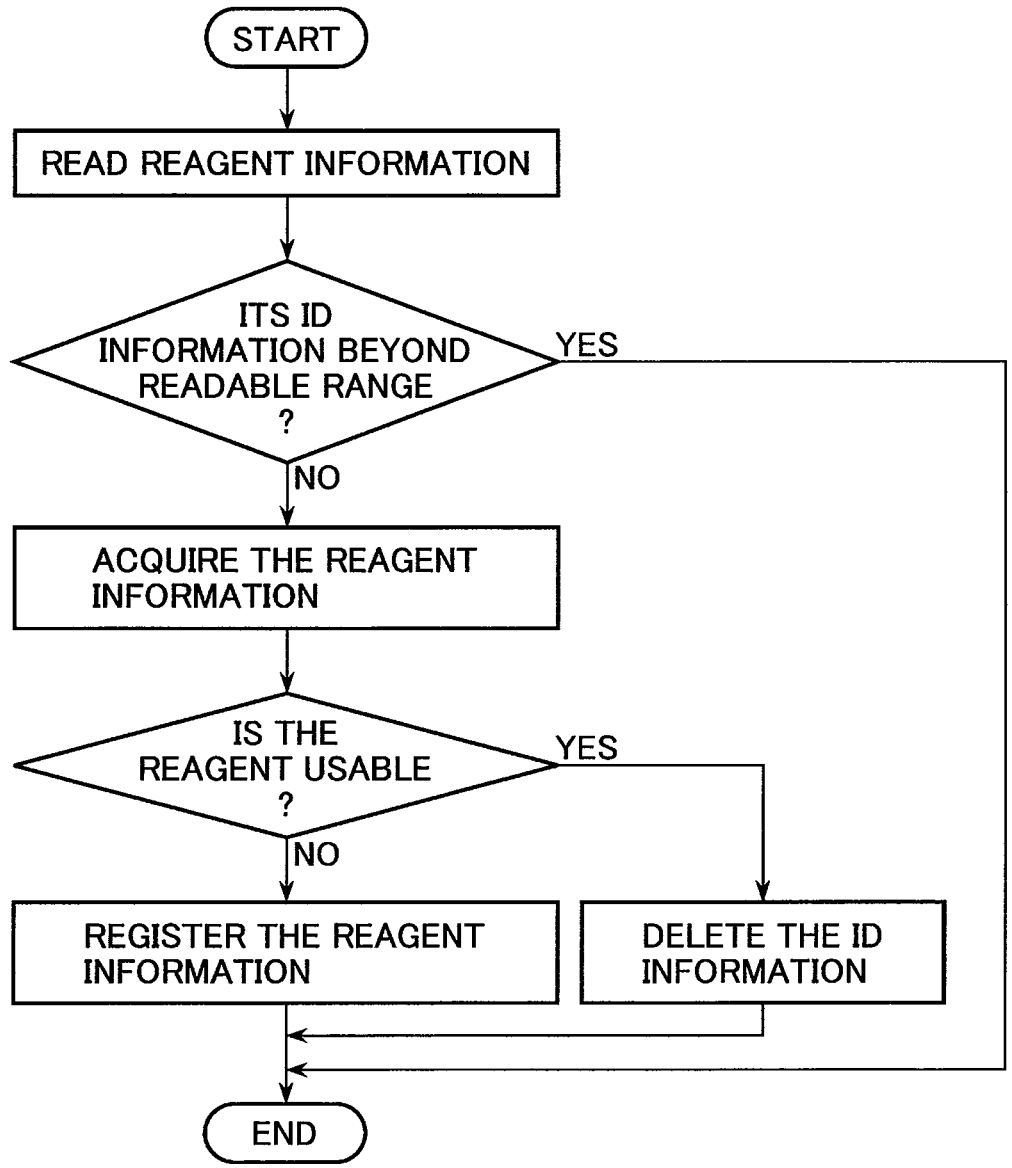
FIG. 4 shows an algorithm for reading reagent information from the storage medium of FIG. 2 and registering that information.

Before an analysis, the automatic analyzer moves the first and second reagent transfer mechanisms 31 and 32 so that a particular reagent vessel 26 is moved to the reading position of the reagent information reader/writer 28. By repeating this step, the reader/writer 28 reads the reagent ID information 41 of all the reagent vessels 26. The ID information 41 read is transmitted through the interface 7 to the microcomputer 1 where the ID information 41 is judged readable or unreadable as in the algorithm of FIG. 4. When the ID information 41 of a particular reagent vessel 26 is unreadable, the analyzer will terminate the process of FIG. 4 for that vessel and will not recognize the ID information 41 as such.

Even if the reader/writer 28 is capable of reading the ID information 41 of a particular reagent vessel 26, the analyzer will not recognize the ID information 41 as such when the ID information 41 is out of its defined value range. In that case, the analyzer outputs an alert message to the effect that the reagent cannot be identified or the reagent ID is wrong.

When the ID information 41 of a particular reagent vessel 26 is readable and within its defined value range, the analyzer acquires the ID information 41 and examines whether the reagent is usable or not. This judgment is made by examining several conditions such as whether the reaming amount is zero, whether the expiration date has passed, and whether the usable period has passed after reagent opening. As illustrated in FIG. 7, a condition code is given to each of these conditions.

When a particular reagent vessel 26 is judged unusable, its reagent ID information 41 is combined with additional information with the use of any one of the storage methods described above. The resultant composite information is overwritten on its reagent information storage medium 33 as new reagent ID information 41.

The present embodiment adopts a non-contact information exchange method by using RFID (Radio-Frequency Identification) tags as the reagent information storage media 33 and an RFID reader as the reagent information reader/writer 28. What matters, however, is that the analyzer is provided with means for deleting information from storage media. Therefore, when one-dimensional barcodes are used as information storage media, the analyzer has only to have means for preventing reagent information from being read from those storage media by blacking out, damaging, or peeling the barcode labels.

The timing for judging a reagent unusable and deleting its ID need not be put before the start of an analysis. Instead, it is possible to put the timing after the date has changed, after the reagent has been used for the analysis, or after the analysis has been completed.

DESCRIPTION OF REFERENCE NUMERALS

1: Microcomputer
2: Memory
3: Hard disk drive
5: Keyboard
6: CRT (display)
7: Interface
11: Photometer
19: Reaction vessel transfer mechanism
20: Reaction vessel
21: Sample vessel
22: Sample vessel transfer mechanism
23: Sample information reader/writer
24: Sample dispenser
25: Reagent dispenser
26: Reagent vessel
28: Reagent information reader/writer
29: Liquid surface detector
30: Sample vessel height detector
31: First reagent transfer mechanism (inner one)
32: Second reagent transfer mechanism (outer one)
33: Reagent information storage medium
41: Reagent ID information
42: Reagent attribute information

The invention claimed is:

1. An automatic analyzer comprising:
an information storage medium on which information can be written;
a liquid vessel to which the information storage medium is attached; and
overwriting means for overwriting the information stored on the information storage medium with information unrecognizable to any analyzers,
wherein information stored on the information storage medium includes liquid ID information for liquid identification,
wherein in the event that the liquid ID information is reagent ID information and the reagent ID information is stored on the information storage medium as a bit array, the overwriting means overwrites all or part of the liquid ID information with values that are out of a defined value range of the liquid ID information, thereby deleting the liquid ID information.

2. The analyzer of claim 1 wherein the reagent ID information is overwritten and rendered unreadable by characters other than the characters constituting the reagent ID information, the former characters being obtained by a bit operation in which the reagent ID information is combined with additional information judged unnecessary, a device ID information of the analyzer that made the judgment, or reagent manufacturer ID information.

3. The analyzer of claim 1 wherein the reagent ID information is overwritten and rendered unreadable by values other than the values constituting the reagent ID information, the former values being obtained by a bit operation in which the reagent ID information is combined with additional information judged unnecessary, a device ID information of the analyzer that made the judgment, or reagent manufacturer ID information.

4. The analyzer of claim 1 wherein the reagent ID information is overwritten and rendered unreadable by information other than the information constituting the reagent ID information and reagent attribute information, the former information being obtained by a bit operation in which the reagent ID information is combined with additional information judged unnecessary, a device ID information of the analyzer that made the judgment, or reagent manufacturer ID information.

* * * * *